(12) United States Patent
Hodge et al.

(10) Patent No.: US 10,035,975 B2
(45) Date of Patent: Jul. 31, 2018

(54) STEARYL AND LAURYL DIMONIUMHYDROXY ALKYL POLYGLUCOSIDES FOR ENHANCED FOOD SOIL REMOVAL

(71) Applicant: Ecolab USA Inc., St. Paul, MN (US)

(72) Inventors: Charles Allen Hodge, Cottage Grove, MN (US); Erin Jane Dahlquist Howlett, West St. Paul, MN (US); Amanda Ruth Blattner, Prior Lake, MN (US)

(73) Assignee: Ecolab USA Inc., Saint Paul, MN (US)

(*) Notice: Subject to any disclaimer, the term of this patent is extended or adjusted under 35 U.S.C. 154(b) by 0 days.

(21) Appl. No.: 15/175,695

(22) Filed: Jun. 7, 2016

(65) Prior Publication Data

US 2016/0289601 A1 Oct. 6, 2016

Related U.S. Application Data

(63) Continuation of application No. 14/501,909, filed on Sep. 30, 2014, now Pat. No. 9,382,505, which is a
(Continued)

(51) Int. Cl.
 *C11D 1/38* (2006.01)
 *C11D 1/62* (2006.01)
 (Continued)

(52) U.S. Cl.
 CPC .............. *C11D 1/62* (2013.01); *C07H 15/04* (2013.01); *C11D 3/2003* (2013.01); *C11D 3/227* (2013.01); *C11D 3/33* (2013.01); *C11D 11/0023* (2013.01)

(58) Field of Classification Search
 CPC ........................................................ C11D 1/62
 (Continued)

(56) References Cited

U.S. PATENT DOCUMENTS 4,488,981 A  12/1984 Urfer et al.
5,179,201 A  1/1993 Oftring et al.
(Continued)

FOREIGN PATENT DOCUMENTS

EP  1027420 B1  5/2004
EP  1077250 B1  1/2005
(Continued)

OTHER PUBLICATIONS

Malik, et al. "Alkaline Hard-Surface Cleaners Containing Alkyl Glycosides" U.S. Statutory Invention Registration No. H468, published May 3, 1988.
(Continued)

*Primary Examiner* — Gregory Webb
(74) *Attorney, Agent, or Firm* — McKee, Voorhees & Sease, PLC

(57) ABSTRACT

A cleaning composition including a primarily $C_{12}$ quaternary functionalized alkyl polyglucoside selected from the group consisting of stearyldimoniumhydroxypropyl laurylglucosides chloride and lauryldimoniumhydroxypropyl cocoglucosides chloride, a water conditioning agent, an acid source, a solvent, and water. In one embodiment, the cleaning composition is substantially free of alkyl phenol ethoxylates. The cleaning composition is capable of removing soils including up to 20% proteins. The cleaning compositions include a biorenewable, environmentally friendly alternative to nonyl phenol ethoxylates and exhibit superior cleaning of food soils.

19 Claims, 2 Drawing Sheets

Related U.S. Application Data continuation of application No. 13/331,990, filed on Dec. 20, 2011, now Pat. No. 8,877,703, which is a continuation-in-part of application No. 12/887,716, filed on Sep. 22, 2010, now Pat. No. 8,389,457.

(51) Int. Cl.

| | | |
|---|---|---|
| *C07H 15/04* | (2006.01) | |
| *C11D 3/20* | (2006.01) | |
| *C11D 3/22* | (2006.01) | |
| *C11D 3/33* | (2006.01) | |
| *C11D 11/00* | (2006.01) | |

(58) Field of Classification Search

USPC ........................................................ 510/504

See application file for complete search history.

(56) References Cited

U.S. PATENT DOCUMENTS

| | | | |
|---|---|---|---|
| 5,342,534 A | 8/1994 | Skrobala et al. | |
| 5,527,483 A | 6/1996 | Kenkare et al. | |
| 5,631,216 A | 5/1997 | Morris et al. | |
| 5,807,816 A | 9/1998 | Cottrell et al. | |
| 6,121,228 A | 9/2000 | Drapier et al. | |
| 6,194,371 B1 | 2/2001 | Donovan et al. | |
| 6,384,010 B1 | 5/2002 | Wagers | |
| 6,627,612 B1 | 9/2003 | O'lenick, Jr. et al. | |
| 6,800,741 B1 | 10/2004 | O'lenick, Jr. | |
| 6,812,202 B2 | 11/2004 | Man et al. | |
| 6,881,710 B1 | 4/2005 | O'lenick, Jr. et al. | |
| 6,927,237 B2 | 8/2005 | Hei et al. | |
| 6,958,315 B1 | 10/2005 | Anderson et al. | |
| 7,008,930 B1 | 3/2006 | O'lenick, Jr. et al. | |
| 7,045,506 B1 | 5/2006 | O'lenick, Jr. et al. | |
| 7,084,129 B1 | 8/2006 | Smith et al. | |
| 7,087,571 B1 | 8/2006 | O'lenick, Jr. et al. | |
| 7,335,627 B1 | 2/2008 | O'lenick, Jr. et al. | |
| 7,341,983 B2 | 3/2008 | Pedersen et al. | |
| 7,375,064 B1 | 5/2008 | O'lenick, Jr. et al. | |
| 7,417,020 B2 | 8/2008 | Fevola et al. | |
| 7,446,086 B2 * | 11/2008 | Bauer .................. | A61K 8/585 |
| | | | 134/25.2 |
| 7,503,332 B2 | 3/2009 | Gross et al. | |
| 7,507,399 B1 | 3/2009 | O'lenick, Jr. et al. | |
| 7,521,413 B2 | 4/2009 | Ochomogo et al. | |
| 7,534,760 B2 | 5/2009 | Johansson et al. | |
| 7,585,830 B2 | 9/2009 | Behler et al. | |
| 7,608,573 B1 | 10/2009 | Scheuing et al. | |
| 7,632,794 B1 * | 12/2009 | Xia ........................ | A01N 43/16 |
| | | | 510/112 |
| 7,754,670 B2 | 7/2010 | Lange et al. | |
| 7,803,746 B2 * | 9/2010 | Luu ........................ | A61K 8/347 |
| | | | 510/130 |
| 8,097,241 B2 * | 1/2012 | Orubor .................... | A61L 11/00 |
| | | | 424/76.6 |
| 2003/0050201 A1 | 3/2003 | Guillou et al. | |
| 2004/0077516 A1 | 4/2004 | Man et al. | |
| 2005/0215449 A1 | 9/2005 | Penninger et al. | |
| 2006/0030512 A1 | 2/2006 | Hart | |
| 2006/0134239 A1 | 6/2006 | Weide et al. | |
| 2007/0032395 A1 | 2/2007 | Fornara et al. | |
| 2007/0259797 A1 | 11/2007 | Fevola et al. | |
| 2007/0265183 A1 | 11/2007 | Meine et al. | |
| 2008/0039357 A1 | 2/2008 | Gross et al. | |
| 2008/0255014 A1 | 10/2008 | Luu et al. | |
| 2009/0047232 A1 * | 2/2009 | Orubor .................... | A61L 11/00 |
| | | | 424/76.6 |
| 2009/0081755 A1 * | 3/2009 | Schmiedel ........... | C11D 3/3945 |
| | | | 435/183 |
| 2009/0156454 A1 | 6/2009 | Schmiedel et al. | |
| 2010/0056416 A1 | 3/2010 | Scheuing et al. | |
| 2012/0046208 A1 * | 2/2012 | Hodge .................. | C11D 1/345 |
| | | | 510/109 |
| 2012/0070341 A1 | 3/2012 | Eder et al. | |
| 2012/0071385 A1 | 3/2012 | Hodge et al. | |
| 2012/0071386 A1 | 3/2012 | Hodge et al. | |
| 2012/0071438 A1 | 3/2012 | Pedersen et al. | |

FOREIGN PATENT DOCUMENTS

| | | |
|---|---|---|
| JP | 2007045991 | 2/2007 |
| WO | 9850510 | 11/1998 |

OTHER PUBLICATIONS

Colonial Chemical, Inc. "Suga Quat Series", www.colonialchem.com (2007) 4 pages.

Ecolab USA Inc. PCT/IB2011/052665 filed Jun. 17, 2011, "International Search Report", dated Feb. 10, 2012.

Ecolab USA Inc. PCT/IB2011/052666, filed Jun. 17, 2011, "International Search Report" dated Feb. 27, 2012.

\* cited by examiner

STEARYL AND LAURYL DIMONIUMHYDROXY ALKYL POLYGLUCOSIDES FOR ENHANCED FOOD SOIL REMOVAL

CROSS-REFERENCE TO RELATED APPLICATION

This application is a Continuation application of U.S. Ser. No. 14/501,909 filed Sep. 30, 2014, which is a Continuation application of U.S. Ser. No. 13/331,990 filed Dec. 20, 2011, now U.S. Pat. No. 8,877,703 issued on Nov. 4, 2014, which is a Continuation-in-Part of U.S. Ser. No. 12/887,716 filed Sep. 22, 2010, now U.S. Pat. No. 8,389,457 issued on Mar. 5, 2013, all of which are hereby incorporated by reference herein in their entirety.

FIELD OF THE INVENTION

The present invention relates to the field of hard surface cleaning compositions. In particular, the invention relates to a hard surface cleaning composition including specific quaternary functionalized alkyl polyglucosides.

BACKGROUND

Conventional detergents used in the ware washing and laundering industries, particularly those intended for institutional use, generally contain alkyl phenol ethoxylates (APEs). APEs are used in detergents as a cleanser and a degreaser for their effectiveness at removing soils containing grease from a variety of surfaces. Commonly used APEs include nonyl phenol ethoxylates (NPE) surfactants.

However, while effective, APEs are disfavored due to environmental concerns. For example, NPEs are formed through the combination of ethylene oxide with nonylphenol (NP). Both NP and NPEs exhibit estrogen-like properties and may contaminate water, vegetation and marine life. NPE is also not readily biodegradable and remains in the environment or food chain for indefinite time periods. There is therefore a need in the art for an environmentally friendly and biodegradable alternative that can replace APEs in hard surface cleaners.

BRIEF SUMMARY OF THE INVENTION

The present invention comprises a hard surface cleaning composition including an environmentally friendly surfactant derived from renewable bio-based resources that works at least as well as NPE. In one embodiment, the present invention is a cleaning composition including specific quaternary functionalized alkyl polyglucosides, stearyl and lauryl dimoniumhydroxypropyl laurylglucosides a water conditioning agent, an acid source, a solvent, and water. The quaternary functionalized alkyl polyglucoside is a primarily $C_{12}$ quaternary functionalized alkyl polyglucoside including a degree of polymerization of 1.8 and 1.0 and an alkyl polyglucoside blend which includes alkylpolyglucosides ranging from $C_8$ to $C_{16}$, but which includes primarily $C_{12}$ alkyl polyglucosides and a degree of polymerization of 1.0. The cleaning composition is substantially free of alkyl phenol ethoxylates.

In another embodiment, the present invention is a method of removing soils from a surface. The method includes diluting a cleaner with water of dilution to form a use solution and contacting the surface with the use solution. In one embodiment, the cleaner includes a quaternary functionalized alkyl polyglucoside, an acid source, a solvent, a water conditioning agent, and water. The quaternary functionalized alkyl polyglucoside includes one of a primarily $C_{12}$ quaternary functionalized alkyl polyglucoside selected from the group consisting of stearyldimoniumhydroxypropyl laurylglucosides chloride, lauryldimoniumhydroxypropyl laurylglucosides chloride, and lauryldimoniumhydroxypropyl cocoglucosides chloride. The use solution is capable of removing soils including up to 20% proteins.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION OF THE PREFERRED EMBODIMENTS

Figure 1:
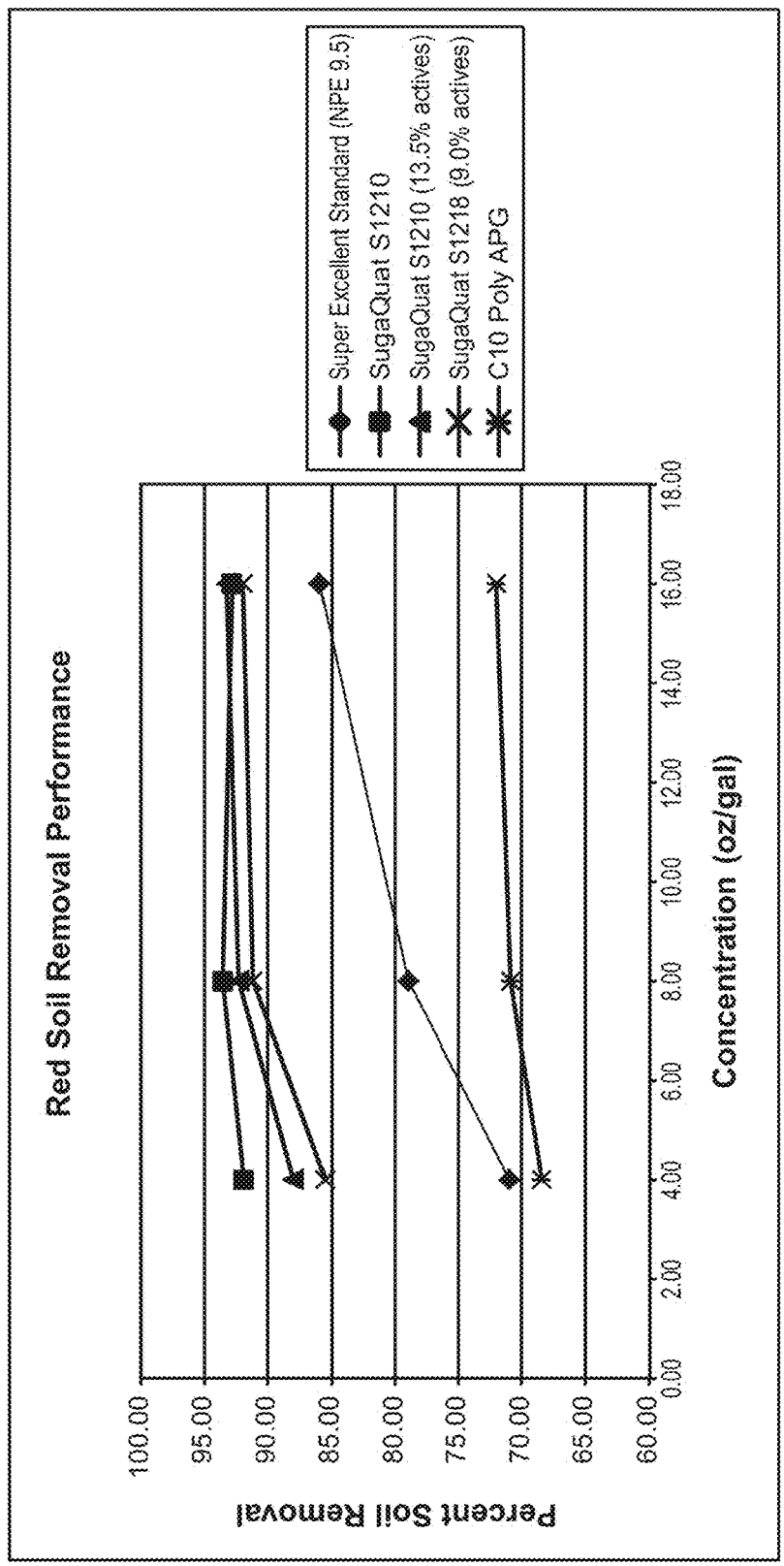
FIG. 1 is a graph showing the concentration and percent of red soil removal for Representative compositions 1-3 with Suga® Quat S 1210 at 18% and 13.5% and Suga® Quat S 1218 at 9% actives with Comparative Example 1 a nonfunctionalized $C_{10}$ alkyl polyglucoside and the control Super Excellent.

Other than in the operating examples, or where otherwise indicated, all numbers expressing quantities of ingredients or reaction conditions used herein are to be understood as being modified in all instances by the term "about".

As used herein, weight percent (wt-%), percent by weight, % by weight, and the like are synonyms that refer to the concentration of a substance as the weight of that substance divided by the total weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

The term "alkyl" refers to a straight or branched chain monovalent hydrocarbon radical having a specified number of carbon atoms. Alkyl groups may be unsubstituted or substituted with substituents that do not interfere with the specified function of the composition and may be substituted once or twice with the same or different group. Substituents may include alkoxy, hydroxy, mercapto, amino, alkyl substituted amino, nitro, carboxy, carbanyl, carbanyloxy, cyano, methylsulfonylamino, or halogen, for example. Examples of "alkyl" include, but are not limited to, methyl, ethyl, n-propyl, isopropyl, n-butyl, s-butyl, t-butyl, n-pentyl, n-hexyl, 3-methylpentyl, and the like.

The term "surfactant" or "surface active agent" refers to an organic chemical that when added to a liquid changes the properties of that liquid at a surface.

"Cleaning" means to perform or aid in soil removal, bleaching, microbial population reduction, rinsing, or combination thereof.

As used herein, the term "substantially free" refers to compositions completely lacking the component or having such a small amount of the component that the component does not affect the effectiveness of the composition. The component may be present as an impurity or as a contaminant and shall be less than 0.5 wt. %. In another embodiment, the amount of the component is less than 0.1 wt. % and in yet another embodiment, the amount of component is less than 0.01 wt. %.

As used herein, the term "ware" includes items such as eating and cooking utensils. As used herein, the term "ware washing" refers to washing, cleaning, or rinsing ware.

As used herein, the term "hard surface" includes showers, sinks, toilets, bathtubs, countertops, windows, mirrors, transportation vehicles, floors, and the like. These surfaces can be those typified as "hard surfaces" (such as walls, floors, bed-pans)

As used herein, a solid cleaning composition refers to a cleaning composition in the form of a solid such as a powder, a particle, an agglomerate, a flake, a granule, a pellet, a tablet, a lozenge, a puck, a briquette, a brick, a solid block, a unit dose, or another solid form known to those of skill in the art. The term "solid" refers to the state of the detergent composition under the expected conditions of storage and use of the solid detergent composition. In general, it is expected that the detergent composition will remain in solid form when exposed to temperatures of up to about 100° F. and greater than about 120° F. A cast, pressed, or extruded "solid" may take any form including a block. When referring to a cast, pressed, or extruded solid it is meant that the hardened composition will not flow perceptibly and will substantially retain its shape under moderate stress or pressure or mere gravity, as for example, the shape of a mold when removed from the mold, the shape of an article as formed upon extrusion from an extruder, and the like. The degree of hardness of the solid cast composition can range from that of a fused solid block, which is relatively dense and hard, for example, like concrete, to a consistency characterized as being malleable and sponge-like, similar to caulking material.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the terms "alkyl phenol ethoxylate free" or "NPE-free" refers to a composition, mixture, or ingredients that do not contain alkyl phenol ethoxylates or phenol-containing compounds or to which the same has not been added. Should alkyl phenol ethoxylates or—alkyl phenol ethoxylate containing compound be present through contamination of a composition, mixture, or ingredients, the amount of the same shall be less than 0.5 wt. %. In another embodiment, the amount of is less than 0.1 wt. % and in yet another embodiment, the amount is less than 0.01 wt. %.

The term "substantially similar cleaning performance" refers generally to achievement by a substitute cleaning product or substitute cleaning system of generally the same degree (or at least not a significantly lesser degree) of cleanliness or with generally the same expenditure (or at least not a significantly lesser expenditure) of effort, or both, when using the substitute cleaning product or substitute cleaning system rather than a alkyl phenol ethoxylate-containing cleaning to address a typical soiling condition on a typical substrate. This degree of cleanliness may, depending on the particular cleaning product and particular substrate, correspond to a general absence of visible soils, or to some lesser degree of cleanliness, as explained in the prior paragraph.

Unless otherwise specified, all formulations reported herein are at 18% actives level.

Quaternary Functionalized Alkyl Polyglucoside Containing Compositions and Methods Employing Them The present invention relates to hard surface cleaning compositions and methods of using the cleaning compositions for cleaning and removing organic soils from a surface. In particular, the cleaning composition is effective at removing soils including proteins, lard and oils from various surfaces. For example, the cleaning composition is effective at removing soils containing up to about 20% protein. The quaternary functionalized alkyl polyglucoside includes one of a primarily $C_{12}$ quaternary functionalized alkyl polyglucoside, preferably at 1.8 and 1.0 degree of polymerization, or a $C_8$ to $C_{16}$ distribution of quaternary alkyl polyglucoside with a majority of $C_{12}$. The quaternary functionalized alkyl polyglucoside component is also a bio-based surfactant, manufactured using renewable carbon and is thus an alternative to synthetic oil based surfactants. In one embodiment, the cleaning compositions are substantially free of alkyl phenol ethoxylates (APEs) such as nonyl phenol ethoxylates (NPEs). Thus, the cleaning compositions provide a green, readily biodegradeable replacement for conventional detergent surfactants. The cleaning compositions can be used in various industries, including, but not limited to: manual and automatic ware washing, food and beverage, vehicle care, quick service restaurants and textile care. In particular, the cleaning compositions can be used in hard-surface cleaning applications, including, for example: bathroom surfaces, dishwashing equipment, food and beverage equipment, vehicles and tabletops. The cleaning compositions can also be used in laundering applications.

In one embodiment, the cleaning composition includes a quaternary functionalized alkyl polyglucoside, a water conditioning agent, an acid source and water. The cleaning compositions of the invention also include the benefit of no required co-surfactant to achieving cleaning at levels that are at least equivalent to and often superior to NPE. The cleaning composition, may optionally include a co-surfactant.

The quaternary functionalized alkyl polyglucoside is a cationic surfactant naturally derived from alkyl polyglucosides and has a sugar backbone. Quaternary functionalized alkyl polyglucosides have the following representative formula:

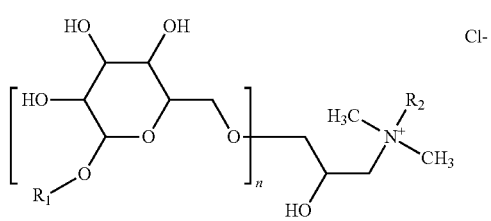

Wherein $R_1$ is an alkyl group having from about 8 to about 22 carbon atoms, and $R_2$ is $CH_3(CH_2)_{n'}$ where n' is an integer ranging from 0-21. Examples of suitable quaternary functionalized alkyl polyglucosides components which can be used in the cleaning compositions according to the present invention include those in which the $R_1$ alkyl moiety contains primarily about 12 carbon atoms, the $R_2$ group is $CH_3$ and n is the degree of polymerization of 1-2. Examples of commercially suitable quaternary functionalized alkyl polyglucosides useful in cleaning compositions of the present invention include but is not limited to: Suga® Quat S 1210 stearyldimoniumhydroxypropyl laurylglucosides chloride, (primarily $C_{12}$ quaternary functionalized alkyl polyglucoside), and Suga® Quat L 8610 lauryldimoniumhydroxypropyl cocoglucosides chloride (primarily $C_{12}$ quaternary functionalized alkyl polyglucoside with a distribution including $C_8$ to $C_{16}$) and Suga® Quat S1218 stearyldimoniumhydroxypropyl laurylglucosides chloride (primarily $C_{12}$ quaternary functionalized alkyl polyglucoside) available from Colonial Chemical, Inc., located in South Pittsburg, Tenn. Applicants have surprisingly found that the cationic functionalized alkyl polyglucoside compounds, known primarily for their use in personal care products, when selected with a carbon chain length of 12, work in cleaning compositions for cleaning food soils, including up to 20% protein.

The water conditioning agent aids in removing metal compounds and in reducing harmful effects of hardness components in service water. Exemplary water conditioning agents include chelating agents, sequestering agents and inhibitors. Polyvalent metal cations or compounds such as a calcium, a magnesium, an iron, a manganese, a molybdenum, etc. cation or compound, or mixtures thereof, can be present in service water and in complex soils. Such compounds or cations can interfere with the effectiveness of a washing or rinsing compositions during a cleaning application. A water conditioning agent can effectively complex and remove such compounds or cations from soiled surfaces and can reduce or eliminate the inappropriate interaction with active ingredients including the nonionic surfactants and anionic surfactants of the invention. Both organic and inorganic water conditioning agents are common and can be used. Inorganic water conditioning agents include such compounds as sodium tripolyphosphate and other higher linear and cyclic polyphosphates species. Organic water conditioning agents include both polymeric and small molecule water conditioning agents. Organic small molecule water conditioning agents are typically organocarboxylate compounds or organophosphate water conditioning agents. Polymeric inhibitors commonly comprise polyanionic compositions such as polyacrylic acid compounds. Small molecule organic water conditioning agents include, but are not limited to: sodium gluconate, sodium glucoheptonate, N-hydroxyethylenediaminetriacetic acid (HEDTA), ethylenediaminetetraacetic acid (EDTA), nitrilotriacetic acid (NTA), diethylenetriaminepentaacetic acid (DTPA), ethylenediaminetetraproprionic acid, triethylenetetraaminehexaacetic acid (TTHA), and the respective alkali metal, ammonium and substituted ammonium salts thereof, ethylenediaminetetraacetic acid tetrasodium salt (EDTA), nitrilotriacetic acid trisodium salt (NTA), ethanoldiglycine disodium salt (EDG), diethanolglycine sodium-salt (DEG), and 1,3-propylenediaminetetraacetic acid (PDTA), dicarboxymethyl glutamic acid tetrasodium salt (GLDA), methylglycine-N—N-diacetic acid trisodium salt (MGDA), and iminodisuccinate sodium salt (IDS). All of these are known and commercially available.

The acid source functions to neutralize the water conditioning agent. Generally, any acid may be used in the composition, but inorganic acids are preferred. Organic acids useful in accordance with the invention include hydroxyacetic (glycolic) acid, citric acid, tartaric acid, lactic acid, ascorbic acid, gallic acid, formic acid, acetic acid, propionic acid, butyric acid, valeric acid, caproic acid, gluconic acid, itaconic acid, trichloroacetic acid, urea sulfate, and benzoic acid, among others. Organic dicarboxylic acids such as oxalic acid, malonic acid, succinic acid, glutaric acid, maleic acid, fumaric acid, adipic acid, and terephthalic acid among others are also useful in accordance with the invention. Any combination of these organic acids may also be used intermixed or with other organic acids which allow adequate formation of the pre-soak composition of the invention. Inorganic acids or mineral acids useful in accordance with the invention and are preferred, these include phosphoric acid, sulfuric acid, sulfamic acid, methylsulfamic acid, hydrochloric acid, hydrobromic acid, hydrofluoric acid, and nitric acid among others. These acids may also be used in combination with other inorganic acids or with those organic acids mentioned above. An acid generator may also be used in the composition to form a suitable acid. For example, suitable generators include calcium phosphate, potassium fluoride, sodium fluoride, lithium fluoride, ammonium fluoride, ammonium bifluoride, sodium silicofluoride, etc. In accordance with the preferred embodiment of the present invention the acid is preferably selected from the group consisting of citric, tartaric, lactic, ascorbic, gallic, and glycolic acid.

An example of a suitable acid source includes, but is not limited to, phosphoric acid. The acid source controls the pH of the resulting solution when water is added to the cleaning composition to form a use solution. The pH of the use solution must be maintained in the neutral to slightly alkaline range in order to provide sufficient detergency properties. This is possible because the soil removal properties of the cleaning composition are primarily due to the quaternary functionalized alkyl polyglucoside, rather than the alkalinity of the cleaning composition. In one embodiment, the pH of the use solution is between approximately 6.5 and approximately 10. In particular, the pH of the use solution is between approximately 8 and approximately 9. If the pH of the use solution is too low, for example, below approximately 6, the use solution may not provide adequate detergency properties. If the pH of the use solution is too high, for example, above approximately 11, the use solution may be too alkaline and attack or damage the surface to be cleaned.

A solvent is often times useful in cleaning compositions to enhance soil removal properties. The cleaning compositions of the invention may include a solvent to adjust the viscosity of the final composition. The intended final use of the composition may determine whether or not a solvent is included in the cleaning composition. If a solvent is included in the cleaning composition, it is usually a low cost solvent such as isopropyl alcohol. A solvent may or may not be included to improve soil removal, handleability or ease of use of the compositions of the invention. Suitable solvents useful in removing hydrophobic soils include, but are not limited to: oxygenated solvents such as lower alkanols, lower alkyl ethers, glycols, aryl glycol ethers and lower alkyl glycol ethers. Examples of other solvents include, but are not limited to: methanol, ethanol, propanol, isopropanol and butanol, isobutanol, ethylene glycol, diethylene glycol, triethylene glycol, propylene glycol, dipropylene glycol, mixed ethylene-propylene glycol ethers, ethylene glycol phenyl ether, and propylene glycol phenyl ether. Substantially water soluble glycol ether solvents include, not are not limited to: propylene glycol methyl ether, propylene glycol propyl ether, dipropylene glycol methyl ether, tripropylene glycol methyl ether, ethylene glycol butyl ether, diethylene glycol methyl ether, diethylene glycol butyl ether, ethylene glycol dimethyl ether, ethylene glycol propyl ether, diethylene glycol ethyl ether, triethylene glycol methyl ether, triethylene glycol ethyl ether, triethylene glycol butyl ether and the like.

The cleaning composition also includes water. It should be appreciated that the water may be provided as deionized water or as softened water. The water provided as part of the concentrate can be relatively free of hardness. It is expected that the water can be deionized to remove a portion of the dissolved solids. That is, the concentrate can be formulated with water that includes dissolved solids, and can be formulated with water that can be characterized as hard water.

In concentrate form the cleaning composition includes a replacement of NPE at 1:1 at the actives level. The cleaning compositions at about 18% activity include between about 40 wt. % and about 80 wt. % quaternary functionalized alkyl polyglucoside component, between about 0 wt % and about 12 wt. % optional co-surfactant, between about 3 wt. % and about 18 wt. % water conditioning agent, between about 0.1 wt. % and about 0.55 wt. % acid source, between about 0 wt % and about 10 wt. % solvent and between about 10 wt. % and about 60 wt. % water. Particularly, the cleaning compositions include between about 45 wt. % and about 75 wt. % quaternary functionalized alkyl polyglucoside component, between about 0 wt. % and about 10 wt. % optional co-surfactant, between about 5 wt. % and about 15 wt. % water conditioning agent, between about 0.3 wt. % and about 0.5 wt. % acid source, between about 0 and about 6 wt. % solvent and between about 15 wt. % and about 50 wt. % water. More particularly, the cleaning compositions include between about 50 wt. % and about 70 wt. % quaternary functionalized alkyl polyglucoside surfactant, if a co-surfactant is used, then between about 7 wt. % and about 10 wt. % co-surfactant, between about 5 wt. % and about 10 wt. % water conditioning agent, between about 0.35 wt. % and about 0.45 wt. % acid source, between about 0 and 4 wt. % solvent and between about 20 wt. % and about 40 wt. % water. In other embodiments, similar intermediate concentrations and use concentrations may also be present in the cleaning compositions of the invention.

In one embodiment, the cleaning compositions of the present invention are substantially free of APEs, making the detergent composition more environmentally acceptable. APE-free refers to a composition, mixture, or ingredients to which APEs are not added. Should APEs be present through contamination of an APE-free composition, mixture, or ingredient, the level of APEs in the resulting composition is less than approximately 0.5 wt. %, less than approximately 0.1 wt %, and often less than approximately 0.01 wt. %.

Additional Functional Materials

The cleaning compositions can include additional components or agents, such as additional functional materials. As such, in some embodiments, the cleaning composition including the quaternary functionalized alkyl polyglucoside may provide a large amount, or even all of the total weight of the cleaning composition, for example, in embodiments having few or no additional functional materials disposed therein. The functional materials provide desired properties and functionalities to the cleaning composition. For the purpose of this application, the term "functional materials" include a material that when dispersed or dissolved in a use and/or concentrate solution, such as an aqueous solution, provides a beneficial property in a particular use. The cleaning preparations containing the quaternary functionalized alkyl polyglucoside and may optionally contain other soil-digesting components, surfactants, disinfectants, sanitizers, acidulants, complexing agents, corrosion inhibitors, foam inhibitors, dyes, thickening or gelling agents, and perfumes, as described, for example, in U.S. Pat. No. 7,341,983, incorporated herein by reference. Some particular examples of functional materials are discussed in more detail below, but it should be understood by those of skill in the art and others that the particular materials discussed are given by way of example only, and that a broad variety of other functional materials may be used. For example, many of the functional materials discussed below relate to materials used in cleaning and/or destaining applications, but it should be understood that other embodiments may include functional materials for use in other applications.

Surfactants

The cleaning composition can contain an additional anionic surfactant component that includes a detersive amount of an anionic surfactant or a mixture of anionic surfactants. Anionic surfactants are desirable in cleaning compositions because of their wetting and detersive properties. The anionic surfactants that can be used according to the invention include any anionic surfactant available in the cleaning industry. Suitable groups of anionic surfactants include sulfonates and sulfates. Suitable surfactants that can be provided in the anionic surfactant component include alkyl aryl sulfonates, secondary alkane sulfonates, alkyl methyl ester sulfonates, alpha olefin sulfonates, alkyl ether sulfates, alkyl sulfates, and alcohol sulfates.

Suitable alkyl aryl sulfonates that can be used in the cleaning composition can have an alkyl group that contains 6 to 24 carbon atoms and the aryl group can be at least one of benzene, toluene, and xylene. A suitable alkyl aryl sulfonate includes linear alkyl benzene sulfonate. A suitable linear alkyl benzene sulfonate includes linear dodecyl benzyl sulfonate that can be provided as an acid that is neutralized to form the sulfonate. Additional suitable alkyl aryl sulfonates include xylene sulfonate and cumene sulfonate.

Suitable alkane sulfonates that can be used in the cleaning composition can have an alkane group having 6 to 24 carbon atoms. Suitable alkane sulfonates that can be used include secondary alkane sulfonates. A suitable secondary alkane sulfonate includes sodium $C_{14}$-$C_{17}$ secondary alkyl sulfonate commercially available as Hostapur SAS from Clariant.

Suitable alkyl methyl ester sulfonates that can be used in the cleaning composition include those having an alkyl group containing 6 to 24 carbon atoms. Suitable alpha olefin sulfonates that can be used in the cleaning composition include those having alpha olefin groups containing 6 to 24 carbon atoms.

Suitable alkyl ether sulfates that can be used in the cleaning composition include those having between about 1 and about 10 repeating alkoxy groups, between about 1 and about 5 repeating alkoxy groups. In general, the alkoxy group will contain between about 2 and about 4 carbon atoms. A suitable alkoxy group is ethoxy. A suitable alkyl ether sulfate is sodium lauryl ether sulfate and is available under the name Steol CS-460.

Suitable alkyl sulfates that can be used in the cleaning composition include those having an alkyl group containing 6 to 24 carbon atoms. Suitable alkyl sulfates include, but are not limited to, sodium lauryl sulfate and sodium lauryl/myristyl sulfate.

Suitable alcohol sulfates that can be used in the cleaning composition include those having an alcohol group containing about 6 to about 24 carbon atoms.

The anionic surfactant can be neutralized with an alkaline metal salt, an amine, or a mixture thereof. Suitable alkaline metal salts include sodium, potassium, and magnesium. Suitable amines include monoethanolamine, triethanolamine, and monoisopropanolamine. If a mixture of salts is used, a suitable mixture of alkaline metal salt can be sodium and magnesium, and the molar ratio of sodium to magnesium can be between about 3:1 and about 1:1.

The cleaning composition, when provided as a concentrate, can include the additional anionic surfactant component in an amount sufficient to provide a use composition having desired wetting and detersive properties after dilution with water. The concentrate can contain about 0.1 wt. % to about 0.5 wt. %, about 0.1 wt. % to about 1.0 wt. %, about 1.0 wt. % to about 5 wt. %, about 5 wt. % to about 10 wt. %, about 10 wt. % to about 20 wt. %, 30 wt. %, about 0.5 wt. % to about 25 wt. %, and about 1 wt. % to about 15 wt. %, and similar intermediate concentrations of the anionic surfactant.

The cleaning composition can contain a nonionic surfactant component that includes a detersive amount of nonionic surfactant or a mixture of nonionic surfactants. Nonionic surfactants can be included in the cleaning composition to enhance grease removal properties. Although the surfactant component can include a nonionic surfactant component, it should be understood that the nonionic surfactant component can be excluded from the detergent composition.

Nonionic surfactants that can be used in the composition include polyalkylene oxide surfactants (also known as polyoxyalkylene surfactants or polyalkylene glycol surfactants). Suitable polyalkylene oxide surfactants include polyoxypropylene surfactants and polyoxyethylene glycol surfactants. Suitable surfactants of this type are synthetic organic polyoxypropylene (PO)-polyoxyethylene (EO) block copolymers. These surfactants include a di-block polymer comprising an EO block and a PO block, a center block of polyoxypropylene units (PO), and having blocks of polyoxyethylene grafted onto the polyoxypropylene unit or a center block of EO with attached PO blocks. Further, this surfactant can have further blocks of either polyoxyethylene or polyoxypropylene in the molecules. A suitable average molecular weight range of useful surfactants can be about 1,000 to about 40,000 and the weight percent content of ethylene oxide can be about 10-80 wt %.

Additional nonionic surfactants include alcohol alkoxylates. A suitable alcohol alkoxylate including linear alcohol ethoxylates such as Tomadol™ 1-5 which is a surfactant containing an alkyl group having 11 carbon atoms and 5 moles of ethylene oxide. Additional alcohol alkoxylates include alkylphenol ethoxylates, branched alcohol ethoxylates, secondary alcohol ethoxylates (e.g., Tergitol 15-S-7 from Dow Chemical), castor oil ethoxylates, alkylamine ethoxylates, tallow amine ethoxylates, fatty acid ethoxylates, sorbital oleate ethoxylates, end-capped ethoxylates, or mixtures thereof. Additional nonionic surfactants include amides such as fatty alkanolamides, alkyldiethanolamides, coconut diethanolamide, lauric diethanolamide, polyethylene glycol cocoamide (e.g., PEG-6 cocoamide), oleic diethanolamide, or mixtures thereof. Additional suitable nonionic surfactants include polyalkoxylated aliphatic base, polyalkoxylated amide, glycol esters, glycerol esters, amine oxides, phosphate esters, alcohol phosphate, fatty triglycerides, fatty triglyceride esters, alkyl ether phosphate, alkyl esters, alkyl phenol ethoxylate phosphate esters, alkyl polysaccharides, block copolymers, alkyl polyglucosides, or mixtures thereof.

When nonionic surfactants are included in the detergent composition concentrate, they can be included in an amount of at least about 0.1 wt. % and can be included in an amount of up to about 15 wt. %. The concentrate can include about 0.1 to 1.0 wt. %, about 0.5 wt. % to about 12 wt. % or about 2 wt. % to about 10 wt. % of the nonionic surfactant.

Amphoteric surfactants can also be used to provide desired detersive properties. Suitable amphoteric surfactants that can be used include, but are not limited to: betaines, imidazolines, and propionates. Suitable amphoteric surfactants include, but are not limited to: sultaines, amphopropionates, amphodipropionates, aminopropionates, aminodipropionates, amphoacetates, amphodiacetates, and amphohydroxypropylsulfonates.

When the detergent composition includes an amphoteric surfactant, the amphoteric surfactant can be included in an amount of about 0.1 wt % to about 15 wt %. The concentrate can include about 0.1 wt % to about 1.0 wt %, 0.5 wt % to about 12 wt % or about 2 wt % to about 10 wt % of the amphoteric surfactant.

The cleaning composition can contain a cationic co-surfactant component that includes a detersive amount of cationic surfactant or a mixture of cationic surfactants. Cationic co-surfactants that can be used in the cleaning composition include, but are not limited to: amines such as primary, secondary and tertiary monoamines with Cis alkyl or alkenyl chains, ethoxylated alkylamines, alkoxylates of ethylenediamine, imidazoles such as a 1-(2-hydroxyethyl)-2-imidazoline, a 2-alkyl-1-(2-hydroxyethyl)-2-imidazoline, and the like; and quaternary ammonium salts, as for example, alkylquaternary ammonium chloride surfactants such as n-alkyl($C_{12}$-$C_{18}$)dimethylbenzyl ammonium chloride, n-tetradecyldimethylbenzylammonium chloride monohydrate, and a naphthylene-substituted quaternary ammonium chloride such as dimethyl-1-naphthylmethylammonium chloride.

Thickening Agents

The viscosity of the cleaning composition increases with the amount of thickening agent, and viscous compositions are useful for uses where the cleaning composition clings to the surface. Suitable thickeners can include those which do not leave contaminating residue on the surface to be treated. Generally, thickeners which may be used in the present invention include natural gums such as xanthan gum, guar gum, modified guar, or other gums from plant mucilage; polysaccharide based thickeners, such as alginates, starches, and cellulosic polymers (e.g., carboxymethyl cellulose, hydroxyethyl cellulose, and the like); polyacrylates thickeners; and hydrocolloid thickeners, such as pectin. Generally, the concentration of thickener employed in the present compositions or methods will be dictated by the desired viscosity within the final composition. However, as a general guideline, the viscosity of thickener within the present composition ranges from about 0.1 wt. % to about 3 wt. %, from about 0.1 wt. % to about 2 wt. %, or about 0.1 wt. % to about 0.5 wt. %.

Bleaching Agents

The cleaning composition may also include bleaching agents for lightening or whitening a substrate. Examples of suitable bleaching agents include bleaching compounds capable of liberating an active halogen species, such as $Cl_2$, $Br_2$, —$OCl^-$ and/or —$OBr^-$, under conditions typically encountered during the cleansing process. Suitable bleaching agents for use in the present cleaning compositions include, for example, chlorine-containing compounds such as a chlorine, a hypochlorite, and chloramine. Exemplary halogen-releasing compounds include the alkali metal dichloroisocyanurates, chlorinated trisodium phosphate, the alkali metal hypochlorites, monochloramine and dichloramine, and the like. Encapsulated chlorine sources may also be used to enhance the stability of the chlorine source in the composition (see, for example, U.S. Pat. Nos. 4,618,914 and 4,830,773, the disclosures of which are incorporated by reference herein for all purposes). A bleaching agent may also be a peroxygen or active oxygen source such as hydrogen peroxide, perborates, sodium carbonate peroxyhydrate, phosphate peroxyhydrates, potassium permonosulfate, and sodium perborate mono and tetrahydrate, with and without activators such as tetraacetylethylene diamine, and the like. The composition can include an effective amount of a bleaching agent. When the concentrate includes a bleaching agent, it can be included in an amount of about 0.1 wt. % to about 60 wt. %, about 1 wt. % to about 20 wt. %, about 3 wt. % to about 8 wt. %, and about 3 wt. % to about 6 wt. %.

Detergent Fillers

The cleaning composition can include an effective amount of detergent fillers, which does not perform as a cleaning agent per se, but cooperates with the cleaning agent to enhance the overall cleaning capacity of the composition. Examples of detergent fillers suitable for use in the present cleaning compositions include sodium sulfate, sodium chloride, starch, sugars, $C_1$-$C_{10}$ alkylene glycols such as propylene glycol, and the like. When the concentrate includes a detergent filler, it can be included in an amount of between about 1 wt % and about 20 wt % and between about 3 wt % and about 15 wt %.

Defoaming Agents

The cleaning composition can include a defoaming agent to reduce the stability of foam and reduce foaming. When the concentrate includes a defoaming agent, the defoaming agent can be provided in an amount of between about 0.01 wt. % and about 3 wt. %.

Examples of defoaming agents that can be used in the composition includes ethylene oxide/propylene oxide block copolymers such as those available under the name Pluronic N3, silicone compounds such as silica dispersed in polydimethylsiloxane, polydimethylsiloxane, and functionalized polydimethylsiloxane such as those available under the name Abil B9952, fatty amides, hydrocarbon waxes, fatty acids, fatty esters, fatty alcohols, fatty acid soaps, ethoxylates, mineral oils, polyethylene glycol esters, alkyl phosphate esters such as monostearyl phosphate, and the like. A discussion of defoaming agents may be found, for example, in U.S. Pat. No. 3,048,548 to Martin et al., U.S. Pat. No. 3,334,147 to Brunelle et al., and U.S. Pat. No. 3,442,242 to Rue et al., the disclosures of which are incorporated by reference herein for all purposes.

Antiredeposition Agents

The cleaning composition can include an anti-redeposition agent for facilitating sustained suspension of soils in a cleaning solution and preventing the removed soils from being redeposited onto the substrate being cleaned. Examples of suitable anti-redeposition agents include fatty acid amides, fluorocarbon surfactants, complex phosphate esters, styrene maleic anhydride copolymers, and cellulosic derivatives such as hydroxyethyl cellulose, hydroxypropyl cellulose, and the like. When the concentrate includes an anti-redeposition agent, the anti-redeposition agent can be included in an amount of between about 0.5 wt % and about 10 wt % and between about 1 wt % and about 5 wt %.

Stabilizing Agents

Stabilizing agents that can be used in the cleaning composition include, but are not limited to: primary aliphatic amines, betaines, borate, calcium ions, sodium citrate, citric acid, sodium formate, glycerine, malonic acid, organic diacids, polyols, propylene glycol, and mixtures thereof. The concentrate need not include a stabilizing agent, but when the concentrate includes a stabilizing agent, it can be included in an amount that provides the desired level of stability of the concentrate. Exemplary ranges of the stabilizing agent include up to about 20 wt %, between about 0.5 wt. % to about 15 wt. % and between about 2 wt. % to about 10 wt. %.

Dispersants

Dispersants that can be used in the cleaning composition include maleic acid/olefin copolymers, polyacrylic acid, and its copolymers, and mixtures thereof. The concentrate need not include a dispersant, but when a dispersant is included it can be included in an amount that provides the desired dispersant properties. Exemplary ranges of the dispersant in the concentrate can be up to about 20 wt. %, between about 0.5 wt. % and about 15 wt. %, and between about 2 wt. % and about 9 wt. %.

Hydrotropes

The compositions of the invention may optionally include a hydrotrope that aides in compositional stability and aqueous formulation. Functionally speaking, the suitable hydrotrope couplers which can be employed are non-toxic and retain the active ingredients in aqueous solution throughout the temperature range and concentration to which a concentrate or any use solution is exposed.

Any hydrotrope coupler may be used provided it does not react with the other components of the composition or negatively affect the performance properties of the composition. Representative classes of hydrotropic coupling agents or solubilizers which can be employed include anionic surfactants such as alkyl sulfates and alkane sulfonates, linear alkyl benzene or naphthalene sulfonates, secondary alkane sulfonates, alkyl ether sulfates or sulfonates, alkyl phosphates or phosphonates, dialkyl sulfosuccinic acid esters, sugar esters (e.g., sorbitan esters), amine oxides (mono-, di-, or tri-alkyl) and $C_8$-$C_{10}$ alkyl glucosides. Preferred coupling agents for use in the present invention include n-octanesulfonate, available as NAS 8D from Ecolab Inc., n-octyl dimethylamine oxide, and the commonly available aromatic sulfonates such as the alkyl benzene sulfonates (e.g. xylene sulfonates) or naphthalene sulfonates, aryl or alkaryl phosphate esters or their alkoxylated analogues having 1 to about 40 ethylene, propylene or butylene oxide units or mixtures thereof. Other preferred hydrotropes include nonionic surfactants of $C_6$-$C_{24}$ alcohol alkoxylates (alkoxylate means ethoxylates, propoxylates, butoxylates, and co-or-terpolymer mixtures thereof) (preferably $C_6$-$C_{14}$ alcohol alkoxylates) having 1 to about 15 alkylene oxide groups (preferably about 4 to about 10 alkylene oxide groups); $C_6$-$C_{24}$ alkylphenol alkoxylates (preferably $C_8$-$C_{10}$ alkylphenol alkoxylates) having 1 to about 15 alkylene oxide groups (preferably about 4 to about 10 alkylene oxide groups); $C_6$-$C_{24}$ alkylpolyglycosides (preferably $C_6$-$C_{20}$ alkylpolyglycosides) having 1 to about 15 glycoside groups (preferably about 4 to about 10 glycoside groups); $C_6$-$C_{24}$ fatty acid ester ethoxylates, propoxylates or glycerides; and $C_4$-$C_{12}$ mono or dialkanolamides. A preferred hydrotrope is sodium xylenesulfonate (SXS).

The composition of an optional hydrotrope can be present in the range of from about 0 to about 25 percent by weight.

Dyes and Fragrances

Various dyes, odorants including perfumes, and other aesthetic enhancing agents may also be included in the cleaning composition. Dyes may be included to alter the appearance of the composition, as for example, any of a variety of FD&C dyes, D&C dyes, and the like. Additional suitable dyes include Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keystone Aniline and Chemical), Metanil Yellow (Keystone Aniline and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (BASF), Pylakor Acid Bright Red (Pylam), and the like.

Fragrances or perfumes that may be included in the compositions include, for example, terpenoids such as citronellol, aldehydes such as amyl cinnamaldehyde, a jasmine such as C1S-jasmine or jasmal, vanillin, and the like.

Adjuvants

The present composition can also include any number of adjuvants. Specifically, the cleaning composition can include stabilizing agents, wetting agents, thickeners, foaming agents, corrosion inhibitors, biocides, hydrogen peroxide, pigments or dyes among any number of other constituents which can be added to the composition. Such adjuvants can be pre-formulated with the present composition or added to the system simultaneously, or even after, the addition of the present composition. The cleaning composition can also contain any number of other constituents as necessitated by the application, which are known and which can facilitate the activity of the present compositions.

EMBODIMENTS OF THE PRESENT COMPOSITIONS

The cleaning composition of the present invention is effective at removing soils containing proteins, lard and oils. In one embodiment, the cleaning composition is effective at removing soils containing up to about 20% protein. Several suitable exemplary liquid concentrate compositions are provided in the following tables.

TABLE 1

Exemplary Composition #1 (18% actives at 1:1 replacement of NPE)

| Component | First Range (Wt %) | Second Range (Wt %) | Third Range (Wt %) |
|---|---|---|---|
| Water | 5-60 | 10-50 | 15-40 |
| Phosphoric Acid (75%) | 0.1-0.55 | 0.3-0.5 | 0.35-0.45 |
| Isopropanol (99%) | 0-5 | 1-4 | 2-4 |
| SXS hydrotrope | 0-25 | 1-20 | 5-15 |
| Quaternary Functionalized Alkyl Polyglucoside (30%) | 40-80 | 45-75 | 50-70 |
| EDTA (40%) | 4-8 | 5-7 | 5.5-6.5 |

TABLE 2

Exemplary Composition #2 (13.5% actives at 0.75:1 replacement of NPE)

| Component | First Range (Wt %) | Second Range (Wt %) | Third Range (Wt %) |
|---|---|---|---|
| Water | 25-75 | 30-65 | 35-55 |
| Phosphoric Acid (75%) | 0.1-0.55 | 0.3-0.5 | 0.35-0.45 |
| Isopropanol (99%) | 0-5 | 1-4 | 2-4 |
| SXS hydrotrope | 0-25 | 1-20 | 5-15 |
| Quaternary Functionalized Alkyl Polyglucoside (30%) | 25-65 | 30-60 | 35-55 |
| EDTA (40%) | 4-8 | 5-7 | 5.5-6.5 |

TABLE 3

Exemplary Composition #3 (9.0% actives at 0.5:1 replacement of NPE)

| Component | First Range (Wt %) | Second Range (Wt %) | Third Range (Wt %) |
|---|---|---|---|
| Water | 30-90 | 40-80 | 50-70 |
| Phosphoric Acid (75%) | 0.1-0.55 | 0.3-0.5 | 0.35-0.45 |
| Isopropanol (99%) | 0-5 | 1-4 | 2-4 |
| Quaternary Functionalized Alkyl Polyglucoside (30%) | 10-60 | 15-50 | 20-40 |
| EDTA (40%) | 4-8 | 5-7 | 5.5-6.5 |

TABLE 4

Exemplary Composition #4 (4.5% actives at 0.25:1 replacement of NPE)

| Component | First Range (Wt %) | Second Range (Wt %) | Third Range (Wt %) |
|---|---|---|---|
| Water | 40-95 | 50-90 | 55-85 |
| Phosphoric Acid (75%) | 0.1-0.55 | 0.3-0.5 | 0.35-0.45 |
| Isopropanol (99%) | 0-5 | 1-4 | 2-4 |
| Quaternary Functionalized Alkyl Polyglucoside (30%) | 5-45 | 7.5-35 | 10-25 |
| EDTA (40%) | 4-8 | 5-7 | 5.5-6.5 |

The concentrate composition of the present invention can be provided as a solid, liquid, or gel, or a combination thereof. In one embodiment, the cleaning compositions may be provided as a concentrate such that the cleaning composition is substantially free of any added water or the concentrate may contain a nominal amount of water. The concentrate can be formulated without any water or can be provided with a relatively small amount of water in order to reduce the expense of transporting the concentrate. For example, the composition concentrate can be provided as a capsule or pellet of compressed powder, a solid, or loose powder, either contained by a water soluble material or not. In the case of providing the capsule or pellet of the composition in a material, the capsule or pellet can be introduced into a volume of water, and if present the water soluble material can solubilize, degrade, or disperse to allow contact of the composition concentrate with the water. For the purposes of this disclosure, the terms "capsule" and "pellet" are used for exemplary purposes and are not intended to limit the delivery mode of the invention to a particular shape.

When provided as a liquid concentrate composition, the concentrate can be diluted through dispensing equipment using aspirators, peristaltic pumps, gear pumps, mass flow meters, and the like. This liquid concentrate embodiment can also be delivered in bottles, jars, dosing bottles, bottles with dosing caps, and the like. The liquid concentrate composition can be filled into a multi-chambered cartridge insert that is then placed in a spray bottle or other delivery device filled with a pre-measured amount of water.

In yet another embodiment, the concentrate composition can be provided in a solid form that resists crumbling or other degradation until placed into a container. Such container may either be filled with water before placing the composition concentrate into the container, or it may be filled with water after the composition concentrate is placed into the container. In either case, the solid concentrate composition dissolves, solubilizes, or otherwise disintegrates upon contact with water. In a particular embodiment, the solid concentrate composition dissolves rapidly thereby allowing the concentrate composition to become a use composition and further allowing the end user to apply the use composition to a surface in need of cleaning. When the cleaning composition is provided as a solid, the compositions provided herein may be altered in a manner to solidify the cleaning composition by any means known in the art. For example, the amount of water may be reduced or additional ingredients may be added to the cleaning composition, such as a solidification agent.

In another embodiment, the solid concentrate composition can be diluted through dispensing equipment whereby water is sprayed at the solid block forming the use solution. The water flow is delivered at a relatively constant rate using mechanical, electrical, or hydraulic controls and the like. The solid concentrate composition can also be diluted through dispensing equipment whereby water flows around the solid block, creating a use solution as the solid concentrate dissolves. The solid concentrate composition can also be diluted through pellet, tablet, powder and paste dispensers, and the like.

The water used to dilute the concentrate (water of dilution) can be available at the locale or site of dilution. The water of dilution may contain varying levels of hardness depending upon the locale. Service water available from various municipalities have varying levels of hardness. It is desirable to provide a concentrate that can handle the hardness levels found in the service water of various municipalities. The water of dilution that is used to dilute the concentrate can be characterized as hard water when it includes at least 1 grain hardness. It is expected that the water of dilution can include at least 5 grains hardness, at least 10 grains hardness, or at least 20 grains hardness.

It is expected that the concentrate will be diluted with the water of dilution in order to provide a use solution having a desired level of detersive properties. If the use solution is required to remove tough or heavy soils, it is expected that the concentrate can be diluted with the water of dilution at a weight ratio of at least 1:1 and up to 1:8. If a light duty cleaning use solution is desired, it is expected that the concentrate can be diluted at a weight ratio of concentrate to water of dilution of up to about 1:256.

In an alternate embodiment, the cleaning compositions may be provided as a ready-to-use (RTU) composition. If the cleaning composition is provided as a RTU composition, a more significant amount of water is added to the cleaning composition as a diluent. When the concentrate is provided as a liquid, it may be desirable to provide it in a flowable form so that it can be pumped or aspirated. It has been found that it is generally difficult to accurately pump a small amount of a liquid. It is generally more effective to pump a larger amount of a liquid. Accordingly, although it is desirable to provide the concentrate with as little water as possible in order to reduce transportation costs, it is also desirable to provide a concentrate that can be dispensed accurately. In the case of a liquid concentrate, it is expected that water will be present in an amount of up to about 90 wt. %, particularly between about 20 wt. % and about 85 wt. %, more particularly between about 30 wt. % and about 80 wt. % and most particularly between about 50 wt. % and about 80 wt. %.

In the case of a RTU composition, it should be noted that the above-disclosed cleaning composition may, if desired, be further diluted with up to about 96 wt. % water, based on the weight of the cleaning composition.

Compositions of the invention may be useful to clean a variety of surfaces. Invention compositions may be used to clean soils on hard surfaces including but not limited to ceramics, ceramic tile, grout, granite, concrete, mirrors, enameled surfaces, metals including aluminum, brass, stainless steel and the like. Compositions of the invention may also be used to clean soiled linens such as towels, sheets, and nonwoven webs. As such, compositions of the invention are useful to formulate hard surface cleaners, laundry detergents, oven cleaners, hand soaps, automotive detergents, and ware washing detergents whether automatic or manual.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

Materials Used

Suga® Quat S 1218: (Stearyldimoniumhydroxypropyl Laurylglucosides Chloride) a primarily $C_{12}$ quaternary functionalized alkyl polyglucoside with a degree of polymerization from 1-2 available from Colonial Chemical, Inc., located in South Pittsburg, Tenn.

Suga® Quat S 1210: (Stearyldimoniumhydroxypropyl Laurylglucosides Chloride) a primarily $C_{12}$ quaternary functionalized alkyl polyglucoside with a degree of polymerization from 1-2 available from Colonial Chemical, Inc., located in South Pittsburg, Tenn.

Suga® Quat L 8610: (Lauryldimoniumhydroxypropyl Cocoglucosides Chloride) a $C_8$ to $C_{16}$ quaternary functionalized alkyl polyglucoside with a degree of polymerization from 1-2 available from Colonial Chemical, Inc., located in South Pittsburg, Tenn.

Super Excellent: a cleaner containing NPE available from Ecolab Inc., Saint Paul, Minn.

A $C_{10}$ nonfunctionalized alkyl polyglucoside test compound.

Red Soil Removal Test

A red soil consisting of lard, oil, protein, and iron (III) oxide (for color) was prepared. About 30 grams of lard was combined with about 30 grams of corn oil, about 15 grams of whole powdered egg, and about 1.5 grams of $Fe_2O_3$.

The back, grooved sides of a plurality of 3"×3" white vinyl tiles were soiled with approximately 0.75 grams of the red soil using a 3" foam brush. The tiles were allowed to dry at room temperature overnight. It is believed that this incubation period allowed the bonds holding the triglycerides and proteins together in the soil to begin to crystallize and interlink. The next day, the tiles were placed into a soaking tray containing about 200 grams of a test composition for about 1 minute.

The soil removal test was conducted using a Precision Force Applicator (PFA), available from Precision Analytical Instruments, Inc., using a synthetic sponge. The PFA is similar to the Gardner Straightline Apparatus except that it is interfaced with a computer to control various parameters, such as, for example speed, number of repetitions, time between cycles, etc. The synthetic sponge was pre-dampened with water with the excess water squeezed out and then saturated with about 50 grams of the test compositions. The tiles were then placed into the PFA with the grain of the tiles parallel to the direction of sponge travel. The tiles were scrubbed with about 2 pounds of pressure with the moistened synthetic sponge for 16 cycles, rotating the tiles 90 degrees every 4 cycles for a complete 360 degree rotation of the tiles. The tiles were then rinsed with city water and dried overnight at room temperature. Hunter Lab L* reflectance of the soiled tiles and washed tiles were measured. The soiled tiles L* reflectance value is represented by the following equation:

$$\text{soiled } L'^* = \frac{1}{3.38 \ln\left(\frac{92.1 - 24.74}{\text{soiled } L^* - 24.74}\right)}$$

where 3.38, 92.1, and 24.74 are constants. The washed tiles L* reflectance value is represented by the following equation:

$$\text{washed } L'^* = \frac{1}{3.38 \ln\left(\frac{92.1 - 24.74}{\text{washed } L^* - 24.74}\right)}$$

The percent soil removal was then calculated as:

$$\text{percent soil removal} = \left(\frac{\text{soiled } L'^* - \text{washed } L'^*}{\text{soiled } L'^*}\right) * 100$$

The compositions were evaluated based on two standards. First, the compositions were evaluated to determine whether an acceptable amount of red soil was removed at low concentrations (i.e., 4 oz/gallon), intermediate concentrations (i.e., 8 oz/gallon) and high concentrations (i.e., 16 oz/gallon). At 18% actives, a composition was considered to perform at an acceptable level if it removed at least about 71% red soil at low concentrations, at least about 79% red soil at intermediate concentrations and at least about 86% red soil at high concentrations.

If the composition removed an acceptable amount of red soil at all concentrations, the compositions were then evaluated to determine whether they performed substantially similarly to, and could act as a suitable replacement for, a commercially known cleaner. Two compositions were considered to behave substantially similarly if the amount of red soil removed was within about 10% at low and high concentrations and within about 15% at intermediate concentrations.

Representative Compositions 1-9, Verses Control

To test the ability of compositions of the present invention and comparative compositions to remove red soil from a surface according to the method described above, various compositions were formulated at 4, 8 and 16 ounce per gallon concentrations at 18%, 13.5%, and 9.0% actives. Each composition was either a 1:1, 0.75:1, 0.5:1, or 0.25:1 replacement of NPE with a quaternary functionalized alkyl polyglucoside.

Representative Composition 1 is a composition of the present invention including Stearyldimoniumhydroxypropyl Laurylglucosides Chloride, a primarily $C_{12}$ quaternary functionalized alkyl polyglucoside with a degree of polymerization from 1-2. In particular, the composition included Suga® Quat S 1210 at 18% actives.

Representative Composition 2 is a composition of the present invention including Stearyldimoniumhydroxypropyl Laurylglucosides Chloride, a primarily $C_{12}$ quaternary functionalized alkyl polyglucoside with a degree of polymerization from 1-2 chloride. In particular, the composition included Suga® Quat S 1210 at 13.5% actives.

Representative Composition 3 is a composition of the present invention including a: Stearyldimoniumhydroxypropyl Laurylglucosides Chloride, a primarily $C_{12}$ quaternary functionalized alkyl polyglucoside with a degree of polymerization from 1-2. In particular, the composition included Suga® Quat S 1218 at 9% actives.

Representative Composition 4 is a composition of the present invention including a: Lauryldimoniumhydroxypropyl Cocoglucosides Chloride a $C_8$ to $C_{16}$ (primarily C12) quaternary functionalized alkyl polyglucoside with a degree of polymerization from 1-2. In particular, the composition included Suga® Quat L 8610 at 18% actives.

Representative Composition 5 is a composition of the present invention including a: Lauryldimoniumhydroxypropyl Cocoglucosides Chloride a $C_8$ to $C_{16}$ (primarily C12) quaternary functionalized alkyl polyglucoside with a degree of polymerization from 1-2. In particular, the composition included Suga® Quat L 8610 at 13.5% actives.

Representative Composition 6 is a composition of the present invention including a: Lauryldimoniumhydroxypropyl Cocoglucosides Chloride a $C_8$ to $C_{16}$ (primarily C12) quaternary functionalized alkyl polyglucoside with a degree of polymerization from 1-2. In particular, the composition included Suga® Quat L 8610 at 9% actives.

Representative Composition 7 is a composition of the present invention including a: Lauryldimoniumhydroxypropyl Cocoglucosides Chloride a $C_8$ to $C_{16}$ (primarily C12) quaternary functionalized alkyl polyglucoside with a degree of polymerization from 1-2. In particular, the composition included Suga® Quat L 8610 at 4.5% actives.

Comparative Example 1 was a composition prepared within the component ranges of the invention, except with $C_{10}$ nonfunctionalized alkyl polyglucoside.

Comparative Example 2 is a composition of the present invention including a: Lauryldimoniumhydroxypropyl Cocoglucosides Chloride a $C_8$ to $C_{16}$ (primarily $C_{12}$) quaternary functionalized alkyl polyglucoside with a degree of polymerization from 1-2. In particular, the composition included Suga® Quat L 8610 at 1.8% actives.

The composition of the control included a commercially known hard surface cleaner, Super Excellent with NPE as a surfactant.

Table 5 provides the concentration and percent of red soil removal for Representative Compositions 1-3 with Suga® Quat S 1210 at 18%, and 13.5% and Suga® Quat S 1218 at 9% actives with Comparative Example 1 a non-functionalized $C_{10}$ alkyl polyglucoside and with the control Super Excellent. The results are depicted graphically in FIG. 1.

TABLE 5

|  | Ratio | Concentration (oz/gal) | Red Soil Removal (%) |
|---|---|---|---|
| Representative Composition 1 Suga® Quat S 1210 (18% actives) | 1:1 | 4<br>8<br>16 | 91.92<br>93.56<br>92.84 |
| Representative Composition 2 Suga® Quat S 1210 (13.5% actives) | 0.75:1 | 4<br>8<br>16 | 88.01<br>92.31<br>93.28 |
| Representative Composition 3 Suga® Quat S 1218 (9.0% actives) | 0.5:1 | 4<br>8<br>16 | 85.52<br>91.21<br>91.98 |
| Comparative Example 1 C10 alkyl polyglucoside | 1:1 | 4<br>8<br>16 | 68.44<br>70.88<br>72.02 |
| Control Super Excellent (NPE 9.5) |  | 4<br>8<br>16 | 71.00<br>79.00<br>86.00 |

Table 6 provides the concentration and percent of red soil removal for Representative Examples 4-7 with Suga® Quat L 8610 at 18%, 13.5%, 9%, 4.5%, and Comparative Example 2 at 1.8% actives with the control Super Excellent. The results are depicted graphically in FIG. 2.

TABLE 6

|  | Ratio | Concentration (oz/gal) | Red Soil Removal (%) |
|---|---|---|---|
| Representative Composition 4 Suga® Quat L 8610 (18% actives) | 1:1 | 4<br>8<br>16 | 86.63<br>90.27<br>91.30 |
| Representative Composition 5 Suga® Quat L 8610 (13.5% actives) | 0.75:1 | 4<br>8<br>16 | 88.74<br>91.99<br>90.20 |
| Representative Composition 6 Suga® Quat L 8610 (9.0% actives) | 0.5:1 | 4<br>8<br>16 | 78.71<br>90.29<br>91.04 |
| Representative Composition 7 Suga® Quat L 8610 (4.5% actives) | 0.25:1 | 4<br>8<br>16 | 78.50<br>85.85<br>93.65 |
| Comparative Example 2 Suga® Quat L 8610 (1.8% actives) | 1:1 | 4<br>8<br>16 | 73.81<br>74.43<br>86.08 |
| Control Super Excellent (NPE 9.5) |  | 4<br>8<br>16 | 71.00<br>79.00<br>86.00 |

Table 5 and FIG. 1 show that Representative Compositions 1-3, which include a primarily $C_{12}$ lauryl or stearyl quaternary functionalized alkyl polyglucoside (Suga® Quat S 1210, and Suga® Quat S 1218), removed red soil at levels that were superior to NPE at 18%, 13.5%, and even 9% actives. This superior soil removal is even more evident when compared to the closely related non-functionalized $C_{10}$ alkyl polyglucoside which removed soil at levels that were inferior to NPE.

Figure 2:
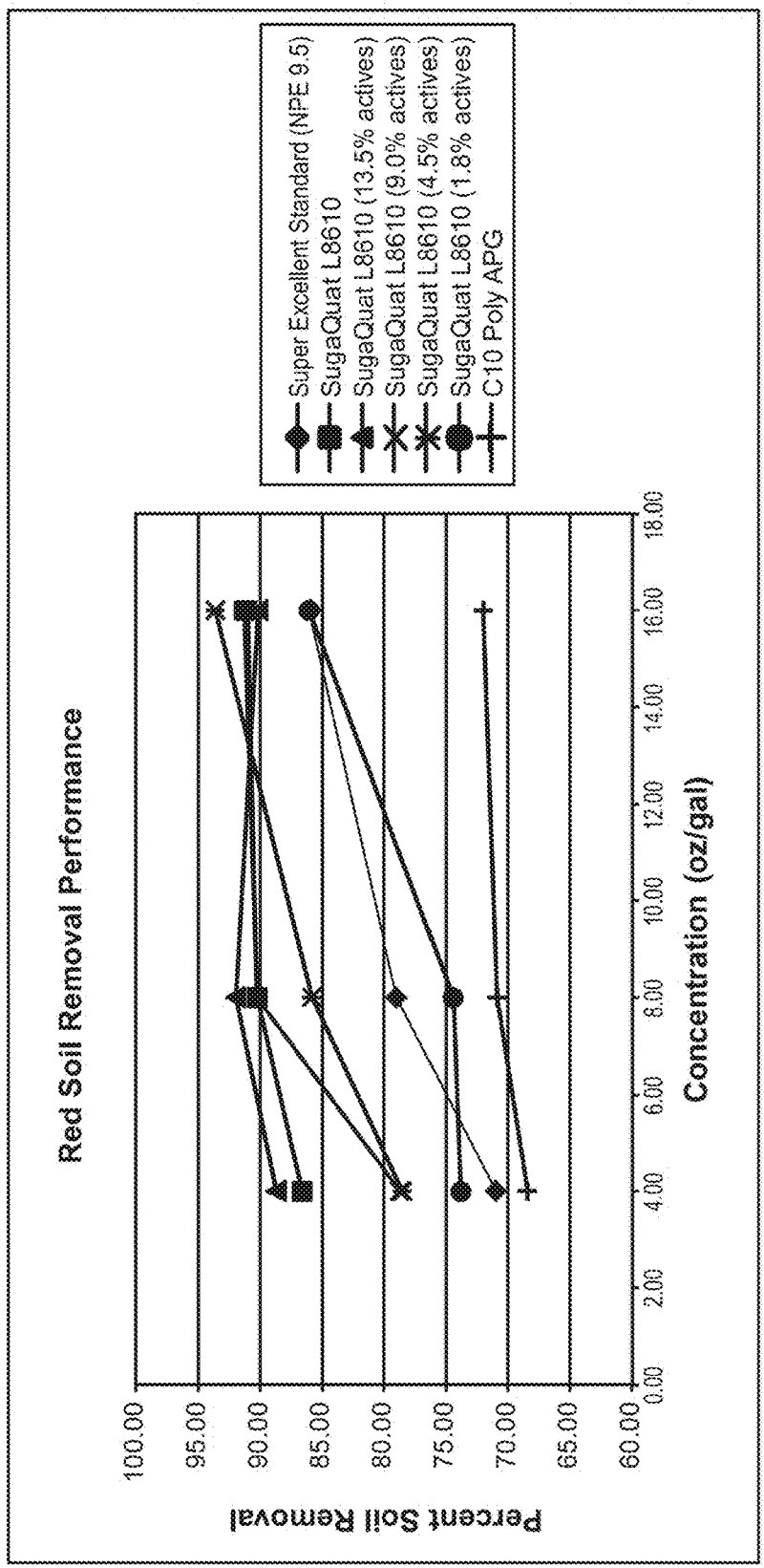
FIG. 2 is a graph showing the concentration and percent of red soil removal for Representative compositions 4-7 with Suga® Quat L 8610 at 18%, 13.5%, 9%, 4.5%, compared with Comparative Example 2 (Suga® Quat L 8610 at 1.8% actives) and compared with the control Super Excellent.

Table 6 and FIG. 2 show that Suga Quat L 8610 also demonstrated superior red soil removal to the control, even at 4.5% actives. At the 1.8% actives the formula still showed soil removal that was similar to NPE. When a $C_{10}$ quaternary functionalized alkyl polyglucoside was used the formula was hazy, with a white precipitate and could not be tested. Surprisingly, the closely related alkyl polyglucoside, (only one carbon difference) a primarily $C_{12}$ carbon chain length was clear, and thus testable and gave superior cleaning results as demonstrated herein.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed:

1. A method of removing soils from a surface comprising:
    contacting a surface with a cleaner,
        wherein the cleaner comprises a primarily $C_{12}$-quaternary functionalized alkyl polyglucoside selected from the group consisting of stearyldimoniumhydroxypropyl laurylglucosides chloride and lauryldimoniumhydroxypropyl cocoglucosides chloride, between about 4% and about 8% by weight a water conditioning agent, a hydrotrope, and between about 5% and about 60% by weight water;
    wherein the surface is soiled.

2. The method of claim 1, further comprising a step of diluting the cleaner with water of dilution at weight ratio of cleaner to water of dilution of up to about 1:256.

3. The method of claim 1, wherein the cleaner comprises less than about 0.5% by weight alkyl phenol ethoxylates.

4. The method of claim 3, wherein the cleaner comprises less than about 0.1% by weight alkyl phenol ethoxylates.

5. The method of claim 1, wherein the cleaner has a pH of between about 6.5 and about 10.

6. The method of claim 1, wherein the soil comprises protein, lard, and/or oil.

7. The method of claim 6, wherein the soil comprises protein.

8. The method of claim 7, wherein the soil comprises up to about 20% protein.

9. The method of claim 1, wherein the cleaner comprises less than about 0.5% by weight alkyl phenol ethoxylates.

10. The method of claim 1, wherein the cleaner comprises less than about 0.1% by weight alkyl phenol ethoxylates.

11. The method of claim 1, wherein the primarily $C_{12}$ quaternary functionalized alkyl polyglucoside constitutes between about 40% and about 80% by weight of the cleaning composition at 18% actives.

12. The method of claim 1, wherein the cleaner further comprises an acid source constituting between about 0.1% and about 0.55% by weight of the cleaner.

13. The method of claim 1, wherein the water conditioning agent comprises ethylenediaminetetraacetic acid tetrasodium salt.

14. The method of claim 1, wherein the hydrotrope is in an amount between about 0.1% and about 25% by weight.

15. A method of removing soils from a surface comprising:
    contacting the surface with a cleaner comprising
        between about 5% and about 80% by weight a primarily $C_{12}$ quaternary functionalized alkyl polyglucoside selected from the group consisting of stearyldimoniumhydroxypropyl laurylglucosides chloride and lauryldimoniumhydroxypropyl cocoglucosides chloride,
        between about 4% and about 8% by weight a water conditioning agent, between about 0.1% and about 0.55% by weight of an acid, between about 0.1% and about 25% by weight of a hydrotrope, and between about 5% and about 60% by weight water, and wherein the cleaner comprises less than about 0.5% by weight alkyl phenol ethoxylates;

wherein the surface is soiled with lard, fat, and/or protein.

16. The method of claim 15, further comprising a step of diluting the cleaner with water of dilution at weight ratio of cleaner to water of dilution of up to about 1:256.

17. The method of claim 16, wherein the soil comprises up to about 20% protein, and wherein the surface is a ware, a hard surface, or a linen.

18. A method of removing soils from a surface comprising:

diluting a with water of dilution at weight ratio of cleaner to water of dilution of up to about 1:256, wherein the cleaner comprises between about 5% and about 80% by weight a primarily $C_{12}$ quaternary functionalized alkyl polyglucoside selected from the group consisting of stearyldimoniumhydroxypropyl laurylglucosides chloride and lauryldimoniumhydroxypropyl cocoglucosides chloride, between about 4% and about 8% by weight a water conditioning agent, between about 0.1% and about 0.55% by weight of an acid, between about 0.1% and about 25% by weight of a hydrotrope, and between about 5% and about 60% by weight water, and wherein the cleaner comprises less than about 0.5% by weight alkyl phenol ethoxylates;

wherein the surface is soiled with lard, fat, and/or protein.

19. The method of claim 18, wherein the surface is a ware, a hard surface, or a linen.

* * * * *